United States Patent
Hellsten et al.

(10) Patent No.: US 8,821,754 B2
(45) Date of Patent: Sep. 2, 2014

(54) ADDITIVE FOR PRESERVING THE FLUIDITY OF FLUIDS CONTAINING GAS HYDRATES

(75) Inventors: Martin Hellsten, Ödsmål (SE); Hans Oskarsson, Stenungsund (SE)

(73) Assignee: Akzo Nobel N.V., Arnhem (NL)

( * ) Notice: Subject to any disclaimer, the term of this patent is extended or adjusted under 35 U.S.C. 154(b) by 874 days.

(21) Appl. No.: 12/293,922

(22) PCT Filed: Mar. 16, 2007

(86) PCT No.: PCT/EP2007/052485
§ 371 (c)(1),
(2), (4) Date: Oct. 14, 2008

(87) PCT Pub. No.: WO2007/107502
PCT Pub. Date: Sep. 27, 2007

(65) Prior Publication Data
US 2009/0114879 A1    May 7, 2009

Related U.S. Application Data

(60) Provisional application No. 60/838,992, filed on Aug. 21, 2006.

(30) Foreign Application Priority Data

Mar. 21, 2006   (EP) ..................................... 06111496

(51) Int. Cl.
| | | |
|---|---|---|
| *C09K 3/00* | (2006.01) |
| *C04B 33/04* | (2006.01) |
| *E21B 43/28* | (2006.01) |
| *C09K 8/54* | (2006.01) |
| *C07C 233/00* | (2006.01) |
| *C07C 235/00* | (2006.01) |
| *C07C 237/00* | (2006.01) |
| *C07C 239/00* | (2006.01) |
| *C07C 9/00* | (2006.01) |
| *F17D 1/16* | (2006.01) |
| *F17D 1/18* | (2006.01) |
| *C09K 8/524* | (2006.01) |
| *C09K 8/52* | (2006.01) |

(52) U.S. Cl.
CPC ............... *C09K 8/52* (2013.01); *C09K 2208/22* (2013.01); *C09K 8/524* (2013.01)
USPC ........ 252/182.29; 507/90; 507/250; 564/123; 564/152; 585/15; 137/13

(58) Field of Classification Search
USPC ........ 507/90, 250; 252/182.29; 564/123, 152; 585/15; 137/13
See application file for complete search history.

(56) References Cited

U.S. PATENT DOCUMENTS

| | | | | |
|---|---|---|---|---|
| 2,889,276 | A * | 6/1959 | Barrett et al. ................. | 507/250 |
| 3,623,979 | A * | 11/1971 | Maddox et al. ............... | 507/243 |
| 4,915,176 | A | 4/1990 | Sugier et al. | |
| 4,973,775 | A | 11/1990 | Sugier et al. | |
| 5,741,758 | A * | 4/1998 | Pakulski ......................... | 507/90 |
| 6,331,508 | B1 * | 12/2001 | Pakulski ......................... | 507/90 |
| 2005/0156137 | A1 * | 7/2005 | Overkempe et al. ............ | 252/70 |

FOREIGN PATENT DOCUMENTS

| | | |
|---|---|---|
| WO | WO 93/25798 | 12/1993 |
| WO | WO 96/34177 | 10/1996 |
| WO | WO 03/008757 A1 | 1/2003 |

OTHER PUBLICATIONS

Nelson et al., Analytical Chemistry 1961 vol. 33 No. 13 pp. 1882-1884.*
NACE Products 2002 {http://www.onepetro.org/mslib/servlet/onepetropreview?id=NACE-02290&soc=NACE} Conference: Corrosion Apr. 7-11, 2002 Denver Co.*
International Search Report for International Application No. PCT/EP2007/052485, Jul. 2, 2007.
OECD Guidelines for Testing of Chemicals 117, "Partition Coefficient (n-octanol/water), High Performance Liquid Chromatography (HPLC) Method;" (Mar. 30, 1989) pp. 1-11.
Edwards, Charles L., "Nonionic Surfactants, Organic Chemistry," Surfactant Science Series, vol. 72 (1998) pp. 1-37.
Oskarsson et al., "New Technique for Evaluating Antiagglomerate Gas-Hydrate Inhibitors in Oilfield Applications," SPE 93075 (2005) pp. 1-10.

* cited by examiner

*Primary Examiner* — Patrick Ryan
*Assistant Examiner* — Aaron Greso
(74) *Attorney, Agent, or Firm* — Norris McLaughlin & Marcus PA

(57) ABSTRACT

The present invention relates to the use of a specific group of alkoxylated and/or acylated non-quaternary nitrogen-containing compounds as anti-agglomerants for gas hydrates.
The invention also relates to a method for inhibiting the agglomeration of gas hydrates in a conduit, and compositions comprising the gas hydrate anti-agglomerant, a corrosion inhibitor and/or a paraffin deposition inhibitor.

7 Claims, No Drawings

ADDITIVE FOR PRESERVING THE FLUIDITY OF FLUIDS CONTAINING GAS HYDRATES

The present invention relates to the use of a group of alkoxylated and/or acylated non-quaternary nitrogen-containing compounds as anti-agglomerants for gas hydrates.

When low molecular hydrocarbon gases such as methane, ethane, propane, butane, and iso-butane are subjected to high pressure in the presence of water, a particular type of ice, so-called gas hydrate, may be formed. The maximum temperature for this formation will depend on the gas pressure. At a sufficiently high pressure the gas hydrate can be stable up to +25° C.

The formation of gas hydrates has important practical implications in oil and gas production, particularly for the transport of natural gas in offshore pipelines where both high pressure and low temperature prevail. If no measures are taken, the pipeline is easily blocked by the formation of gas hydrates.

It has long been common practice to add either methanol or ethylene glycol to the gas/water or gas/water/oil stream in order to decrease the freezing point of the gas/water mixture. This method, which is called thermodynamic inhibition, will prevent primary formation of gas hydrates. However, it necessitates an addition of 10-60% of the amount of water present in the fluid, depending on the temperature and the gas pressure. This high level of addition will also make it necessary to recover the additive at the destination point. Altogether, this makes thermodynamic inhibition a rather expensive operation.

This in turn has led to the search for additives that can be used in much lower dosages, and this search has resulted in two principally different modes of action, kinetic inhibition and dispersion. In both cases the normal dosage of the additive is 1-3% of the water present in the gas/water or gas/water/oil stream.

Kinetic Inhibition of the Formation of Gas Hydrates

Kinetic inhibitors are products which delay the initial nucleation of gas hydrates. Kinetic inhibitors thus are only effective for a limited period of time, which is a disadvantage. These products normally are polymers, and several classes of polymers suitable as kinetic inhibitors have been described in WO 93/25798.

Dispersion of Gas Hydrates

When dispersants are used, the formation of small crystals of gas hydrates occurs, but the agglomeration of these crystals is prevented. This is mainly expected to be due to adsorption of the dispersant on the surfaces of initially formed crystals of gas hydrate. The dispersants typically are surface-active agents i.e. they contain at least one hydrophilic (polar) and at least one hydrophobic (nonpolar, oleophilic) group. The dispersant will adsorb with its polar end toward the gas hydrate crystal, turning its nonpolar, hydrocarbon end outwards. The crystals thus are made oleophilic and can easily be dispersed in the liquid hydrocarbon phase. Dispersants thus are only effective when such a liquid oil phase is present. This will normally be the case in the pipeline from the production well to the first treatment station, when the fluid stream contains both gas and oil as well as water. The adsorbed layer of dispersants on the crystals will also prevent them from growing together into large aggregates, which otherwise may cause complete blockage of the pipe line. This property of the dispersants has resulted in their usually being named anti-agglomerants, and this term will be used throughout this application.

In U.S. Pat. No. 4,915,176 a method of transporting a hydrate forming fluid is disclosed, where an additive is injected into the fluid for reducing the tendency to agglomeration of the hydrates so as to obtain hydrates in the dispersed form. The additives used in the working examples are fatty acid diethanolamides having different alkyl chain lengths, sodium dioctylsulfosuccinate, and sorbitan monolaurate.

In WO 96/34177 quaternary ammonium surfactants are described where at least two butyl, pentyl or iso-pentyl groups are attached to the nitrogen atom, which also carries one or two long alkyl glycol ether chains. Some products with this configuration have been shown to be good gas hydrate anti-agglomerants. Their main drawback is that they are not readily biodegraded. The production process for these types of compounds also contains several steps and thus is rather time-consuming.

WO 03/008757 discloses alkoxylated quaternary ammonium compounds containing ester groups as anti-agglomerants. These compounds are not readily biodegradable either.

In U.S. Pat. No. 6,331,508 a method for controlling the formation of gas hydrate crystals in a fluid mixture is disclosed, where a polyoxyalkylenediamine is added to the mixture in an amount effective to prevent and/or inhibit crystal growth. The preferred compounds have the general formula

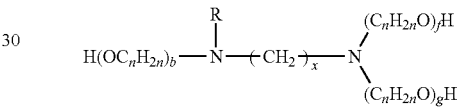

wherein R is an alkyl group having 1-20 carbon atoms, x=1-4, n=2 or 3, and b+f+g=3-30, preferably 20-30. In the working example Ethoduomeen T/25 (ex Akzo Nobel) is used. This compound is a N-(tallow alkyl)propylenediamine that has been reacted with 15 moles of ethylene oxide; thus this is a compound according to the formula above wherein x is 3, n is 2, and b+f+g=15. Also propoxylated compounds with b+f+g=30 were suggested. However, propoxylated products containing large amounts of propylene oxide units will exhibit a high log $P_{ow}$ (see further below for a definition of log $P_{ow}$), since the solubility in water will be rather low, and further the biodegradability will be poor.

In U.S. Pat. No. 4,973,775 a process for delaying the formation and/or reducing the agglomeration tendency of gas hydrates is disclosed wherein hydroxy-carbylamides and polyhydroxycarbylamides are used. Suggested compounds are described by the general formulae (1), (2), and (3)

(1)

(2)

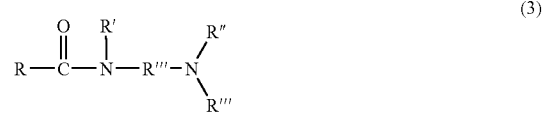

(3)

wherein R—C═O is a radical of the carboxylic acid and comprises 4 to 28 carbon atoms, R', R", and R'" are hydroxycarbyl radicals and R"" is an alkylenic radical of the type $C_nH_{2n}$, and n is a whole number equal to at least 1. Only compounds according to formula (2) are disclosed, such as coconut diethanolamide, ethoxylated coconut diethanolamide, rapeseed diethanolamide or diethanolamides from other acids.

Although various options are provided to overcome the problem of agglomeration, there is still a need for improved anti-agglomerants for gas hydrates.

The aim of the present invention is to find new anti-agglomerants for gas hydrates that are efficient in seawater, brackish and/or fresh water, and have a better biodegradability and are more economically attractive than previously known compounds.

It has now surprisingly been found that a surface-active non-quaternary nitrogen-containing compound with 1-5, preferably 1-4, more preferably 1-3, and most preferably 1 or 2 nitrogen atoms, which compound has at least one hydrophobic group with 6-24, preferably 8-22, and most preferably 8-18 carbon atoms, and where the hydrophobic group is connected to the remainder of the molecule by an amine moiety, an ether moiety or an amide moiety, provided that when the hydrophobic group is connected by means of an amide moiety to the remainder of the molecule, the compound must contain a total of at least 2 nitrogen atoms;

which compound optionally contains 1-12, preferably 2-10 —$CH_2CH_2O$— groups and/or 1-6 hydroxyalkyl groups with 3-4 carbon atoms; and which compound has at least one C2-C3, preferably C2, acyl group and/or at least one hydroxyalkyl group with 3-4 carbon atoms, preferably with 3 carbon atoms; which compound is selected from the group below consisting of compounds IA, IB, IC, II, and III, or a salt thereof;

is an efficient anti-agglomerant for gas hydrates in both salt and fresh water and at the same time has a better biodegradability than the prior art compounds. A further advantage is that these compounds also have the ability to act as corrosion inhibitors. According to an unproven theory, it is believed that the essential acyl, hydroxypropyl, and hydroxybutyl groups have an improved adhesion to the gas hydrate surface, and thereby facilitate dispersion and prevent agglomeration.

The surface-active non-quaternary nitrogen-containing compound is selected from the group of non-quaternary nitrogen-containing compounds having the following general formulae IA, IB, IC, II, and III, viz.

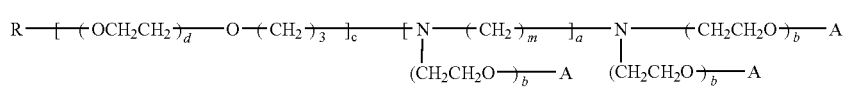
(IA)

wherein R is a $C_6$-$C_{24}$, preferably a $C_8$-$C_{22}$, and most preferably a $C_8$-$C_{18}$ hydrocarbyl group; m is 2 or 3, preferably 3; a=0-4, preferably 0-3, and most preferably 0 or 1; b is at least 1 at each position; Σb on average is 2-12, preferably 2-10; c is 0 or 1; d on average is 0-5, preferably 0; each A is independently selected from H, —C(═O)$CH_3$, —C(═O)$CH_2CH_3$, C1-C3 alkyl groups, —[$CH_2CH(X)O$]$_e$H, and —[$CH_2CH(X)O$]$_e$—C(═O)$CH_3$ wherein X is —$CH_3$ or —$CH_2CH_3$, preferably —$CH_3$, e is 1-3, and the sum of all e in the molecule is at most 6 on average; provided that at least one of groups A is —[$CH_2CH(X)O$]$_e$H, —[$CH_2CH(X)O$]$_e$—C(═O)$CH_3$—C(═O)$CH_3$ or —C(═O)$CH_2CH_3$;

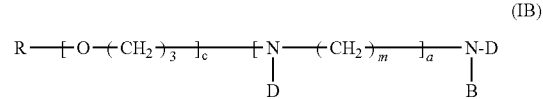
(IB)

wherein B is independently selected from —[$CH_2CH(X)O$]$_e$H, —[$CH_2CH(X)O$]$_e$—C(═O)$CH_3$ or H; each D is independently selected from H, a hydrocarbyl group with 1-24 carbon atoms, preferably 1-3 carbon atoms, —[$CH_2CH(X)O$]$_e$H or —[$CH_2CH(X)O$]$_e$—C(═O)$CH_3$;

provided that at least one of groups D or group B is —[$CH_2CH(X)O$]$_e$H or —[$CH_2CH(X)O$]$_e$—C(═O)$CH_3$;

m, a, c, e, Σe and X are as defined for IA; and R is a hydrocarbyl group with 6-24 carbon atoms, preferably 6-18, and most preferably 6-15 carbon atoms, provided that when all D and B are a group —[$CH_2CH(X)O$]$_e$H, c=0, m=3, and a=1-4, then log $P_{ow}$ for the molecule is at most 3.

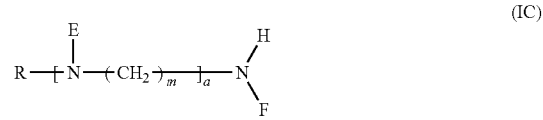
(IC)

wherein R is a hydrocarbyl group having 6-24, preferably 8-22, and most preferably 8-18 carbon atoms; m is 2 or 3, preferably 3; a=0-4, preferably 0-3, and most preferably 1; E is $C_1$-$C_3$ alkyl, —C(═O)$CH_3$ or —C(═O)$CH_2CH_3$; and F is —C(═O)$CH_3$ or —C(═O)$CH_2CH_3$.

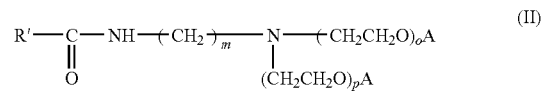
(II)

wherein R'C(═O)— is an acyl group with 6-24, preferably 8-22, and most preferably 8-18 carbon atoms; o=0-3, preferably 1-2; p=0-3, preferably 0-2; Σ(o+p) on average is 0-6, preferably 1-4; m is 2 or 3, preferably 2; and each A is independently selected from H, —[$CH_2CH(X)O$]$_e$H, —[$CH_2CH(X)O$]$_e$—C(═O)$CH_3$—C(═O)$CH_3$, —C(═O)$CH_2CH_3$, and C1-C3 alkyl groups, provided that at least one of groups A is —[$CH_2CH(X)O$]$_e$H, —[$CH_2CH(X)O$]$_e$—C(═O)$CH_3$—C(═O)$CH_3$ or —C(═O)$CH_2CH_3$, wherein X, e and Σe have the same meaning as for IA;

and

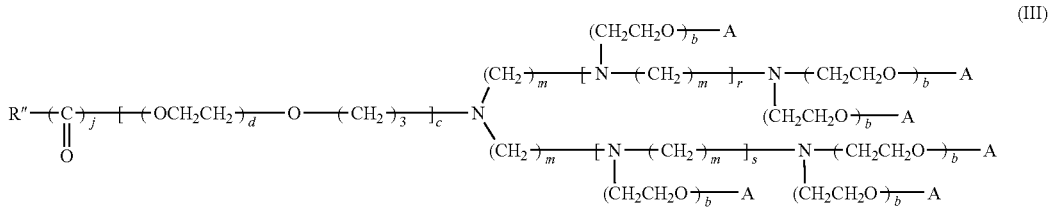

wherein r and s independently are 0-2 provided Σr+s=0-2; and j is 0 or 1, provided that when j=1, then c=0 and R"=R', and when j=0, then R"=R, and provided that at least one of A is —[CH$_2$CH(X)O]$_e$H, —[CH$_2$CH(X)O]$_e$—C(=O)CH$_3$—C(=O)CH$_3$ or —C(=O)CH$_2$CH$_3$, wherein X, e, and Σe have the same meaning as for IA; R, c, d, b, Σb, m, and A are as defined for IA, and R'C(=O)— is as defined for (II);
or a salt of any of compounds IA, IB, IC, II or III; or any combination thereof.

Preferred structures of formula IA are those where all groups A are —CH$_2$CH(CH$_3$)OH or those where all groups A are —C(=O)CH$_3$.

Thus, one embodiment of the invention comprises compounds according to the formulae

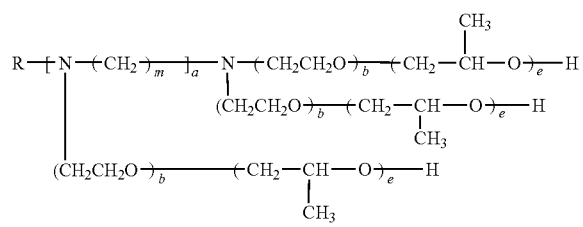

wherein R is a hydrocarbyl group of 6-24, preferably 8-22, and most preferably 8-18 carbon atoms, m is 2 or 3, preferably 3, a is 0 or 1, the sum of b on average is 2-6, and the sum of e is 2 or 3, and

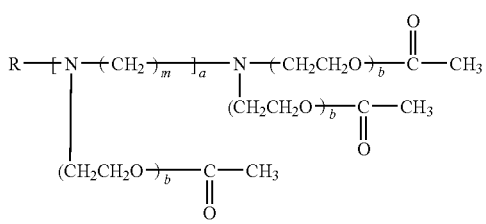

wherein R is a hydrocarbyl group of 6-24, preferably 8-22, and most preferably 8-18 carbon atoms, m is 2 or 3, a is 0 or 1, and the sum of b is 2-6.

Another embodiment comprises compounds having formula IB, wherein R is a C$_6$-C$_{15}$ hydrocarbyl group, c is 0, m is 3, a is 1, B and D are independently selected from the groups —CH$_2$CH(X)O]$_e$H and —[CH$_2$CH(X)O]$_e$—C(=O)CH$_3$, and the sum of e on average is 3-6.

Preferred structures of formula IC are those wherein a=1, the group F is —C(=O)CH$_3$, and the group E is C1-C3 alkyl or —C(=O)CH$_3$.

Thus, a further embodiment of the invention comprises compounds having the formula

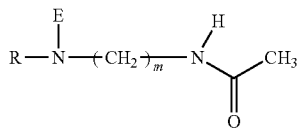

wherein R is an alkyl group having 6-24, preferably 8-22, and most preferably 8-18 carbon atoms, m is 2 or 3, preferably 3, and E is C1-C3 alkyl preferably methyl, or —C(=O)CH$_3$.

Preferred surface-active non-quaternary nitrogen-containing compounds of formula II are selected from the group of compounds having the following general formulae

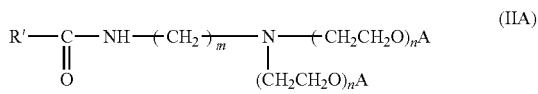

wherein n is at least 1 at each position and Σn on average is 2-4, m is 2 or 3, preferably 2, R'(C=O)— and A are as defined for II except that X is —CH$_3$, provided that at least one of A is —[CH$_2$CH(CH$_3$)O]$_e$H,
—[CH$_2$CH(CH$_3$)O]$_e$—C(=O)CH$_3$ or —C(=O)CH$_3$,
wherein e and Σe are as defined for II;
and

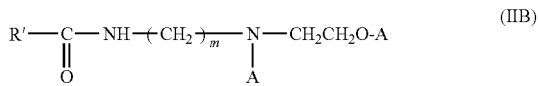

wherein m is 2 or 3, preferably 2; R'(C=O)— and A are as defined for II except that X is —CH$_3$, provided that at least one of A is —[CH$_2$CH(CH$_3$)O]$_e$H, —[CH$_2$CH(CH$_3$)O]$_e$—C(=O)CH$_3$ or —C(=O)CH$_3$; wherein X, e, and Σe have the same meaning as for IA;
and salts of any of compounds IIA and IIB.

Thus, still another embodiment of the invention comprises compounds IIA having the formula

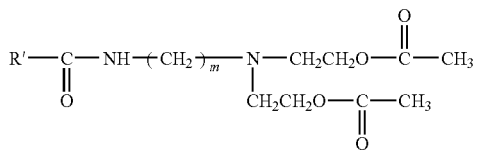

wherein R'(C=O)— is an acyl group having 6-24, preferably 8-22, and most preferably 8-18 carbon atoms, and m is 2 or 3, preferably 2; and compounds IIB having the formula

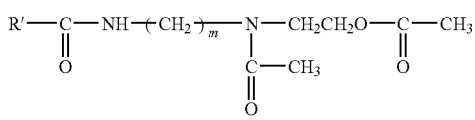

wherein R'(C=O)— is an acyl group having 6-24, preferably 8-22, and most preferably 8-18 carbon atoms, and m is 2 or 3, preferably 2.

Preferred surface-active non-quaternary nitrogen-containing compounds of formula III have the formula

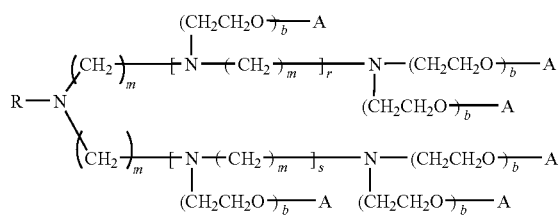

(IIIA)

wherein r and s independently are 0-1, preferably both r and s are 0; R, b, $\Sigma b$, m, and A are as defined for IA except that X is $-CH_3$, provided that at least one of A is $-[CH_2CH(CH_3)O]_eH$, $-[CH_2CH(CH_3)O]_e-C(=O)CH_3$ or $-C(=O)CH_3$, wherein e and $\Sigma e$ are as defined for IA; or a salt of IIIA.

Any combination of IA, IB, IC, IIA, IIB, and IIIA or their salts may also be used. The compounds having these formulae or their salts were found to be biodegradable, efficient anti-agglomerants for gas hydrates.

In a further embodiment, the anti-agglomerant has a low $\log P_{ow}$ ($=\log K_{ow}$) preferably $\leq 3$, more preferably 2 or lower, since substances with a log POW higher than 3 are liable to bioaccumulate. This value can be either experimentally measured or theoretically calculated, and is derived from the partitioning of a compound between the two phases n-octanol and water. The partition coefficient (P) is defined as the ratio of the equilibrium concentrations of a dissolved substance in a two-phase system consisting of two largely immiscible solvents; in the case of n-octanol and water the $P_{ow}$ value (=the octanol-water partition coefficient) of a compound is:

$P_{ow} = (C_{n\text{-}octanol}/C_{water})$ where $C_{n\text{-}octanol}$ and $C_{water}$ are the equilibrium concentrations of the compound in the octanol and water phases, respectively. Due to the emulsifying properties of many surfactants, log $P_{ow}$ normally is theoretically calculated for these kinds of products. For an introduction to the calculation of $P_{ow}$ see Annex to the *OECD Guideline for Testing of Chemicals* 117 and references therein.

For the compounds IB it is essential that log $P_{ow}$ is at most 3.

The above compounds are obtainable by methods well known in the art. Compounds of formula IA are obtainable by first ethoxylating a suitable alkyl amine, alkyl polyamine, alkyl etheramine or alkyl etherdiamine, such as a primary (fatty alkyl)monoamine, (fatty alkyl)aminopropyl amine, 3-[(fatty alkyl)oxy]propyl amine or N-[3-(fatty alkyl)oxy]-1,3-propane diamine, and then propoxylating and/or butoxylating and/or acetylating the ethoxylated product. The number of moles of ethylene oxide reacting with the amine compound need not be an integer and represents the number average degree of polymerization of the ethylene oxide in the product (see *Nonionic Surfactants: Organic Chemistry in Surfactant Science Series* Volume 72, 1998, p 1ff, edited by Nico M. van Os; Marcel Dekker, Inc). Products of formula IA may be added to the water phase as such or as a salt with an acid, preferably as a carboxylic acid salt thereof. Any lower carboxylic acid salt is suitable, and acetic acid salts are especially preferred. Also salts of IA with mineral acids may suitably be used, such as the chlorides, sulfates, and phosphates.

Compounds of formula IB are obtainable by propoxylating and/or butoxylating a suitable alkyl amine, alkyl polyamine or alkyl etheramine. Also here the product is preferably added as a carboxylic acid salt, but salts with mineral acids are also suitable for use.

Compounds of formula IC are obtainable by acetylating a N-(fatty alkyl)-1,3-propylenediamine or N-(fatty alkyl),N—(C1-3 alkyl)-1,3-propylenediamine.

Compounds of formula IIA are obtainable by producing an amide from a fatty acid and aminoethyl ethanolamine or aminopropyl ethanolamine, ethoxylating the amide, and then propoxylating and/or acetylating the ethoxylated amide.

Compounds of formula IIB are obtainable by producing an amide from a fatty acid and aminoethyl ethanolamine or aminopropyl ethanolamine and then directly propoxylating and/or acetylating the amide. Also for both IIA and IIB the product is preferably added as a salt.

Compounds of formula IIIA are obtainable by first ethoxylating a suitable alkyl polyamine containing a tertiary mono (fatty alkyl)amino group and then propoxylating and/or acetylating the ethoxylated product. The product is preferably added as a salt.

Suitable alkyl amines and alkyl polyamines that can be used as starting materials for compounds of formulae IA and IB are (fatty alkyl)monoamines according to formula $R1NH_2$, wherein R1 is an aliphatic group having 6-24 carbon atoms; (fatty alkyl) diamines according to formula $R2NHCH_2CH_2CH_2NH_2$, wherein R2 is an aliphatic group having 6-24 carbon atoms (also suitable as starting material for IC); and linear (fatty alkyl)triamines according to formula $R3NHCH_2CH_2CH_2NHCH_2CH_2CH_2NH_2$, wherein R3 is an aliphatic group having 6-24 carbon atoms.

Suitable alkyl etheramines or alkyl etherdiamines that can be used as starting materials for compounds of formulae IA and IB are alkyl etheramines according to formula $R4O(CH_2CH_2CH_2)NH_2$ and alkyl etherdiamines according to formula $R5O(CH_2CH_2CH_2)NH(CH_2CH_2CH_2)NH_2$, wherein R4 and R5 are aliphatic groups having 6-24 carbon atoms.

Suitable alkyl polyamines that can be used as starting materials for compounds of formulae III and IIIA are branched (fatty alkyl)triamines (Y-triamines) of formula $R6N(CH_2CH_2CH_2NH_2)_2$, wherein R6 is an aliphatic group having 6-24, preferably 8-22, carbon atoms, or branched (fatty alkyl)pentaamines of formula $R7N(CH_2CH_2CH_2NHCH_2CH_2CH_2NH_2)_2$, wherein R7 is an aliphatic group having 6-24, preferably 8-22 carbon atoms.

Suitable alkyl etherpolyamines that can be used as starting materials for compounds of formula III are those of formula $R8O(CH_2CH_2CH_2)N(CH_2CH_2CH_2NH_2)_2$, wherein R8 is an aliphatic group having 6-24, preferably 8-22 carbon atoms.

Examples of suitable fatty amines for use as starting materials for compounds of formulae IA and IB are n-hexyl amine, 2-ethylhexyl amine, n-octyl amine, 2-propylheptyl amine, n-decyl amine, n-dodecyl amine, (coco alkyl)amine, n-tetradecyl amine, n-hexadecyl amine, n-octadecyl amine, oleyl amine, (tallow alkyl)amine, (rapeseed alkyl)amine, (soya alkyl)amine, erucyl amine, N-(n-decyl)-trimethylene diamine, N-(n-dodecyl)-trimethylene diamine, N-(coco alkyl)-trimethylene diamine, N-(rapeseed alkyl)-trimethylene diamine, N-(soya alkyl)-trimethylene diamine, N-(tallow alkyl)-trimethylene diamine, N-erucyl trimethylene diamine, N-(n-decyl)-N'-(3-aminopropyl)-1,3-propane diamine, N-(n-dodecyl)-N'-(3-aminopropyl)-1,3-propane diamine, N-(coco alkyl)-N'-(3-aminopropyl)-1,3-propane diamine, N-(rapeseed alkyl)-N'-(3-aminopropyl)-1,3-propane diamine, N-(soya alkyl)-N'-(3-aminopropyl)-1,3-propane diamine, N-oleyl-N'-(3-aminopropyl)-1,3-propane diamine, N-(tallow alkyl)-N'-(3-amino-propyl)-1,3-propane diamine, N-erucyl-N'-(3-aminopropyl)-1,3-propane diamine, N-(3-aminopropyl)-N'-[3-(9-decylamino)propyl]-1,3-propane diamine, N-(3-aminopropyl)-N'-[3-(9-dodecylamino)propyl]-1,3-propane diamine, N-(3-aminopropyl)-N'-[3-(9-(coco alkyl)amino)propyl]-1,3-propane diamine, N-(3-aminopropyl)-N'-[3-(9-(rapeseed alkyl)amino)propyl]-1,3-propane diamine, N-(3-aminopropyl)-N'-[3-(9-(soya alkyl)amino)propyl]-1,3-propane diamine, N-(3-aminopropyl)-N'-[3-(9-octadecenylamino)propyl]-1,3-propane diamine, N-(3-aminopropyl)-N'-[3-(9-(tallow alkyl)amino)propyl]-1,3-propane diamine, and N-(3-aminopropyl)-N'-[3-(9-erucylamino)propyl]-1,3-propane diamine.

Examples of suitable fatty diamines for use as starting materials for compounds of formula IC are N-(2-ethylhexyl)-trimethylene diamine, N-(n-octyl)-trimethylene diamine, N-(n-decyl)-trimethylene diamine, N-(n-dodecyl)-trimethylene diamine, N-(n-tetradecyl)-trimethylene diamine, N-(coco alkyl)-trimethylene diamine, N-(n-hexadecyl)-trimethylene diamine, N-oleyl-trimethylene diamine, N-(rapeseed alkyl)-trimethylene diamine, N-(soya alkyl)-trimethylene diamine, N-(tallow alkyl)-trimethylene diamine, N-erucyl-trimethylene diamine, N-(n-octyl)-N-methyl aminopropylamine, N-(2-ethylhexyl)-N-methyl aminopropylamine, N-(n-decyl)-N-methyl aminopropylamine, N-(n-dodecyl)-N-methyl aminopropylamine, N-(coco alkyl)-N-methyl aminopropylamine, N-(n-tetradecyl)-N-methyl amino-propylamine, N-oleyl-N-methyl aminopropylamine, N-(rapeseed alkyl)-N-methyl aminopropylamine, N-(soya alkyl)-N-methyl aminopropylamine, and N-(tallow alkyl)-N-methyl aminopropylamine.

Examples of suitable alkyl etheramines and alkyl etherdiamines for use as starting materials for compounds of formulae IA and IB are 3-(n-octyloxy)propyl amine, 3-[2-(ethylhexyl)oxy]propyl amine, 3-(n-decyloxy)propyl amine, 3-[2-(propylheptyl)oxy]propyl amine, 3-(dodecyloxy)propyl amine, 3-[(coco alkyl)oxy]propyl amine, 3-[(rapeseed alkyl)oxy]propyl amine, 3-[(soya alkyl)oxy]propyl amine, 3-(octadecenyloxy)propyl amine, 3-[(tallow alkyl)oxy]-propyl amine, 3-(erucyloxy)propyl amine, N-[3-(2-(ethylhexyl)oxy)propyl]-1,3-propane diamine, N-[3-(n-octyloxy)propyl]-1,3-propane diamine, N-[3-(n-decyloxy)propyl]-1,3-propane diamine, N-[3-(2-(propylheptyl)oxy)propyl]-1,3-propane diamine, N-[3-(tridecyloxy)propyl]-1,3-propane diamine, and ether mono- and diamines based on $C_6$-$C_{24}$ alcohols that have been ethoxylated with up to 5 moles of ethylene oxide.

Examples of fatty acids for use as starting materials for the amides of compounds of formulae II, IIA, IIB, and III are hexanoic acid, 2-ethylhexanoic acid, n-octanoic acid, n-decanoic acid, n-dodecanoic acid, coco fatty acid, oleic acid, rapeseed fatty acid, soya fatty acid, tallow fatty acid, tall oil fatty acid, and erucic acid.

Examples of (fatty alkyl)polyamines that can be used as starting materials for compounds of formulae III and IIIA are N,N-bis(3-aminopropyl)hexyl amine, N N-bis(3-aminopropyl)(2-ethylhexyl)amine, N N-bis(3-aminopropyl)n-octyl amine, N,N-bis(3-aminopropyl)decyl amine, N,N-bis(3-aminopropyl)(2-propyl-heptyl)amine, N,N-bis(3-aminopropyl) dodecyl amine, N,N-bis(3-aminopropyl)-(coco alkyl)amine, N,N-bis(3-aminopropyl)tetradecyl amine, N,N-bis(3-aminopropyl)hexadecyl amine, N,N-bis(3-aminopropyl)stearyl amine, N,N-bis(3-aminopropyl)(rapeseed alkyl)amine, N,N-bis(3-aminopropyl)(tallow alkyl)amine, N,N-bis(3-aminopropyl)(soya alkyl)amine, N,N-bis(3-aminopropyl)oleyl amine, and N,N-bis(3-aminopropyl)erucyl amine.

Examples of (fatty alkyl)etherpolyamines that can be used as starting materials for compounds of formula III are N-[3-(n-octyloxy)propyl]-N,N-bis(3-amino-propyl)amine, N-[3-(n-dodecyloxy)propyl]-N,N-bis(3-aminopropyl)amine, N-[3-(tridecyloxy)propyl]-N,N-bis(3-aminopropyl)amine, N-[3-[(tallow alkyl)oxy)]-propyl]-N,N-bis(3-aminopropyl) amine, and N-[3-(octadecenyloxy)propyl]-N,N-bis(3-aminopropyl)amine.

The acylation reaction can be performed with an acid, an acid anhydride or an acyl chloride. The acetylation reaction is most conveniently performed with acetic anhydride, but also, e.g., acetic acid or acetyl chloride may be used. The ethoxylation and propoxylation reactions are well known in the art. Normally all primary and secondary amino groups are alkoxylated in a first step in the absence of any catalyst, to obtain amino groups fully substituted by hydroxyalkyl groups, i.e. normally no hydrogens remain on the nitrogen atoms. If further alkylene oxide is to be added, typically an alkali metal hydroxide is used as a catalyst, preferably KOH. However, the choice of catalyst is not critical, and there are many catalysts known to the person skilled in the art that could equally well be used. Wherever the degree of alkoxylation is discussed, the numbers referred to are molar average numbers.

The present invention also relates to a method for inhibiting the agglomeration of gas hydrates in a conduit, where the conduit contains a flowing mixture comprising hydrocarbons with 1-4 carbon atoms and water and where hydrates are formed from the hydrocarbons and water, the method comprising the steps:
  a) adding to the mixture an anti-agglomerant as defined in formulae IA, IB, IC, II, and III in an amount that is effective to inhibit the agglomeration of hydrates at the prevailing temperature and pressure in the conduits;
  b) flowing the mixture containing the anti-agglomerant through the conduit.

The concentrations of the anti-agglomerants are at least 0.05%, preferably at least 0.5%, by weight of the water phase, and at most 10%, preferably at most 5%, and most preferably at most 3%, by weight of the water phase. The exact amount of anti-agglomerant to be used depends, inter alia, on the structure of the anti-agglomerant, the water quality, the pressures applied, and the actual composition of the gas and/or oil. The anti-agglomerants of the invention in addition to their dispersing ability also have other useful properties, such as corrosion inhibiting ability. The anti-agglomerant is preferably added in the well head in a composition that may also contain other corrosion inhibitors and paraffin deposition inhibitors. Such a composition suitably contains
  a) 1 part by weight of the gas hydrate anti-agglomerant as defined in formulae IA, IB, IC, II, and III, and
  b) 0.0001-0.1, preferably 0.001-0.05 parts by weight of a corrosion inhibitor and/or a paraffin deposition inhibitor.

In a final embodiment of the invention, the present anti-agglomerant is used in combination with other compounds that are used in compositions wherein gas hydrates are potentially formed, such as corrosion inhibitors and other additives. Examples of suitable corrosion inhibitors are tallow amines, N-(tallow alkyl)-trimethylene diamines, imidazolines, and quaternary amines, and examples of suitable paraffin deposition inhibitors are alcohol esters of alpha-olefin maleic anhydride copolymers, ethylene vinyl acetate copolymers, and alcohol esters of polyacrylic acid. Other additives that may be present in the compositions are foam depressors, such as silicone-containing compounds, glycol and polyglycols, kinetic inhibitors, such as the polymers or co-polymers of N-vinyl-2-pyrrolidone as described in WO 1993/025798, biocides, metal complexants, such as citric acid, solubilizing agents, and additives for stabilizing the dispersion, as well as other dispersants.

The following embodiments illustrate the invention and should not be construed as limiting the scope thereof.

EXAMPLES

General

The technique used for evaluating the anti-agglomerants is described in detail in "New Technique for Evaluating Anti-agglomerate Gas-Hydrate Inhibitors in Oilfield Applications", SPE 93075, 2005 SPE International Symposium on Oilfield Chemistry, Houston, Tex., Feb. 2-4.

Principle:

The complete multicell system consists of a high-pressure vessel containing the multicell test unit, a cooling unit, a stirrer drive, a sensor interface unit, and a computer system. The high-pressure vessel is connected to two gas cylinders containing pressurized hydrocarbon gas (87.9% methane, 7.7% ethane, 3.1% propane, and 1.3% isobutane) and nitrogen. Thus, in an experimental run each test cell will be subjected to the same gas mixture, temperature, and pressure. Each cell has a magnetic bar stirrer and the rotation of the stirrer is monitored by the sensor and recorded. When gas hydrate crystals are formed in a cell, there will be a change in viscosity or flow behaviour and there will be a change in the lag of the stirrer bar. Each time the magnetic bar passes a certain point, an optical pulse is recorded. The lag is measured as the difference between the position of the lower drive magnets and the stirrer in the cell. When the viscosity gets too high, as is the case when larger aggregates of gas hydrates are formed, the magnetic stirrer will either stop completely, in which case the signal will be zero, or start "skipping", which will create an unstable/random signal, and this will be shown in the recorded graph.

Each cell is also equipped with a temperature sensor.

In the Tables of Examples 1 and 2 below the following notations have been used.

EO=ethyleneoxy unit

PO=propyleneoxy unit

0=the compound does not work as an anti-agglomerant

1=the compound initially works as an anti-agglomerant, but not throughout the whole test 2=the compound works as an anti-agglomerant throughout the whole test (for notations 0, 1, and 2, see further explanations in Example 2)

—=test not performed

Example 1

In Table 1 the results from multicell screening of some anti-agglomerants are collected.

The cells are loaded with 1 ml of water/inhibitor mixture and 2.5 ml of Sleipner condensate (=crude oil obtained from the Sleipner oilfield of Statoil). Nitrogen is first applied to expel most of the air, and then hydrocarbon gas is admitted until a constant pressure of 100 bars is reached.

During the whole test, the mixtures were continuously stirred at 120 rpm. The temperature was first lowered from about 20° C. to 4° C. in about 1.5 hours, then kept at 4° C. for about two hours, and finally reheated again to 20° C. in about 1.5 hours. When the stirrer works all the time, the compound is considered to work well as an anti-agglomerant, whereas if the stirrer bar stops, the compound is considered not to work as an anti-agglomerant during the prevailing conditions. The tests were performed both in seawater and in fresh water and at different concentrations of the anti-agglomerants.

TABLE 1

Tests multicell screening

| | Compound | Seawater 1.0% | Seawater 1.5% | Fresh water 1.5% | Fresh water 2.5% |
|---|---|---|---|---|---|
| A. | Oleyl amine + 2EO + 2PO, quaternized with $CH_3Cl$ (Comparison) | — | 2 | 0 | — |
| B. | (Coco alkyl)amine + 2EO (Comparison) | 0 | 0 | — | — |
| C. | (Coco alkyl)amine + 4 EO; acetic acid salt (Comparison) | 0 | 0 | — | — |
| D. | Oleyl amine + 2EO; acetic acid salt (Comparison) | 0 | — | — | — |
| 1. | Oleyl amine + 2EO + 2PO; acetic acid salt | — | 2 | — | — |
| 2. | Erucyl amine + 2EO + 2PO; acetic acid salt | — | 2 | 2 | — |
| 3. | (Coco alkyl)amine + 2EO + 2PO; acetic acid salt | 2 | 2 | — | — |
| 4. | N-(n-octyl)-trimethylene diamine + 3PO; acetic acid salt (log Pow = 0.84)* | — | 2 | — | — |
| 5. | Oleyl amine + 2EO, diester with acetic acid; acetic acid salt | 0 | 2 | 0 | 0 |
| 6. | N-oleyl-trimethylene diamine + 3EO, triesterified with acetic anhydride; acetic acid salt | — | 2 | — | 2 |
| 7. | Monoamide between oleic acid and aminoethyl ethanolamine + 1EO, diesterified with acetic anhydride; acetic acid salt | 2 | — | — | — |
| 8. | Monoamide between oleic acid and aminoethyl ethanolamine, amidated with acetic anhydride | 2 | 2 | 2 | — |

TABLE 1-continued

Tests multicell screening

| | | Seawater | | Fresh water | |
|---|---|---|---|---|---|
| | Compound | 1.0% | 1.5% | 1.5% | 2.5% |
| 9. | N,N-bis(3-aminopropyl)(tallow alkyl)amine, diamidated with acetic anhydride | 0 | 2 | — | — |
| 10. | N-oleyl-trimethylene diamine diamidated with acetic anhydride | — | 2 | — | — |
| 11. | N-(n-octyl)-trimethylene diamine di-amidated with acetic anhydride | — | 2 | — | — |
| 12. | N-(coco alkyl)-trimethylene diamine diamidated with acetic anhydride | — | 2 | — | — |
| 13. | N-(tallow alkyl)-N-methyl aminopropylamine monoamidated with acetic anhydride | — | 2 | — | — |

*the log $P_{ow}$ values in Tables 1 and 2 were calculated using Models developed by the U.S. EPA Office of Pollution Prevention and Toxics and the Syracuse Research Corporation (U.S. EPA (United States Environmental Protection Agency). 2004. Estimation Program Interface (EPI) Suite (EPISuite ™) Version 3.12, Aug. 17, 2004).

The products according to the invention are at least as good or better anti-agglomerants in the screening test than the references A, B, C, and D and at the same time more easily biodegradable than A. Note also that the references B and C, which are (coco alkyl)amine ethoxylates, are not effective in this test as anti-agglomerants for gas hydrates, whereas product 3, which is a (coco alkyl)amine that has first been ethoxylated and then propoxylated, works excellently as an anti-agglomerant.

Example 2

In Table 2 the results from multicell shut-in and restart of some anti-agglomerants are collected. This test is more challenging than the test in Example 1.

The cells are loaded in the same way as above, but hydrocarbon gas is admitted until the constant stated pressure is reached.

In this experiment the test cells were stirred at 120 rpm for one hour at 20° C. and the stated pressure. The stirring was then stopped and the autoclave cooled to 4° C. in about 1.5 hours. The cells were then kept at 4° C. for a minimum of twelve hours before the driving magnets were restarted at 120 rpm. They were then kept running for about two hours at 4° C. before the cells were reheated to 20° C. in about 1.5 hours.

Three different events could then be observed:

The stirrer did not start at all until the temperature had been increased so much that the gas hydrate had melted, which normally happened at about 15° C. This is marked as 0 in the tables.

The stirrer started but stopped again after a short period. This is marked as 1 in the tables.

The stirrer started and kept on running continuously. This is marked as 2 in the tables.

TABLE 2

Tests multicell shut-in

| | Seawater (70 bar) | | Fresh water (70 bar) | |
|---|---|---|---|---|
| Compound | 1.5% | 2.5% | 2.0% | 2.5% |
| 1. Oleyl amine + 2EO + 2PO; acetic acid salt | 2** | 1 | 1 | 1 |
| 3. (Coco alkyl)amine + 2EO + 2PO; acetic acid salt | 0 | 1 | 2 | — |

TABLE 2-continued

Tests multicell shut-in

| | Seawater (70 bar) | | Fresh water (70 bar) | |
|---|---|---|---|---|
| Compound | 1.5% | 2.5% | 2.0% | 2.5% |
| 6. N-oleyl-trimethylene diamine + 3EO, triesterified with acetic anhydride; acetic acid salt | 0 | 1 | — | 2 |
| 10. N-oleyl-trimethylene diamine diamidated with acetic anhydride | 0 | 2 | — | 2 |
| 14. N-(2-ethylhexyl)-trimethylene diamine, diamidated with acetic anhydride | 0 | 0 | — | 2 |
| 15. N-(2-ethylhexyl)-trimethylene diamine + 3PO; acetic acid salt (log Pow* = 0.77) | — | 2 | — | 1 |

*the log $P_{ow}$ values in Tables 1 and 2 were calculated using Models developed by the U.S. EPA Office of Pollution Prevention and Toxics and the Syracuse Research Corporation (U.S. EPA (United States Environmental Protection Agency). 2004. Estimation Program Interface (EPI) Suite (EPISuite ™) Version 3.12, Aug. 17, 2004).
**measured at 100 bar The anti-agglomerants according to the invention have an essential anti-agglomerating effect in sea-, brackish and/or fresh water and at the same time are more easily biodegradable.

The invention claimed is:

1. An anti-agglomerant for gas hydrates, which comprises at least one surface-active non-quaternary nitrogen-containing compound having the following formulae

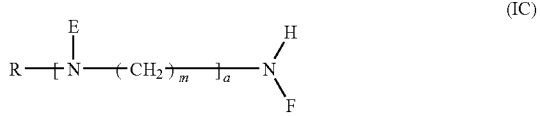

(IC)

where R is a $C_6$-$C_{24}$ hydrocarbyl group, m is 3, a=1, E is C1-C3 alkyl, —C(=O)CH$_3$ or —C(=O)CH$_2$CH$_3$, and F is —C(=O)CH$_3$ or —C(=O)CH$_2$CH$_3$;

or a salt thereof.

2. A method for inhibiting the agglomeration of gas hydrates in a conduit, where the conduit contains a flowing mixture comprising hydrocarbons with 1-4 carbon atoms and water and where hydrates are formed from the hydrocarbons and water; the method comprising the steps:

a) adding to the mixture an anti-agglomerant which comprises at least one surface-active non-quaternary nitrogen-containing compound having the formula

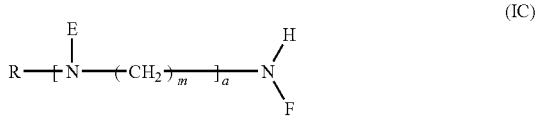
(IC)

where R is a $C_6$-$C_{24}$ hydrocarbyl group, m is 3, a=1, E is C1-C3 alkyl, —C(=O)$CH_3$ or —C(=O)$CH_2CH_3$, and F is —C(=O)$CH_3$ or —C(=O)$CH_2CH_3$;

or a salt thereof in an amount of 0.05-10%, based on the water content of the hydrocarbon/water mixture b) flowing the mixture containing the anti-agglomerant through the conduit.

3. The method according to claim 2 wherein a corrosion inhibitor and/or a paraffin deposition inhibitor are added to the hydrocarbon/water mixture.

4. A composition containing
  a) 1 part by weight of the gas hydrate anti-agglomerant as defined in claim 1; and
  b) 0.0001-0.1 parts by weight of a corrosion inhibitor and/or a paraffin deposition inhibitor.

5. The method of claim 2 wherein 0.05-10% anti-agglomerate is added to said mixture.

6. The method of claim 2 wherein 0.5-3% anti-agglomerate is added to said mixture.

7. The method of claim 2 wherein the anti-agglomerant is added in an amount of at least 0.5% based on the water content.

* * * * *